(12) United States Patent
Imanzahrai

(10) Patent No.: US 6,642,243 B1
(45) Date of Patent: Nov. 4, 2003

(54) MIGRAINE MEDICINE AND METHOD FOR TREATING SAME

(76) Inventor: Ashkan Imanzahrai, 1642 Nord La., San Jose, CA (US) 95125

(*) Notice: Subject to any disclaimer, the term of this patent is extended or adjusted under 35 U.S.C. 154(b) by 10 days.

(21) Appl. No.: 09/593,238

(22) Filed: Jun. 14, 2000

Related U.S. Application Data

(60) Provisional application No. 60/144,973, filed on Jul. 22, 1999.

(51) Int. Cl.$^7$ .............................................. A61K 31/522
(52) U.S. Cl. .................. 514/263.34; 514/165; 514/630; 514/730; 514/741
(58) Field of Search ................................ 514/165, 630, 514/730, 741, 263.34

(56) References Cited

U.S. PATENT DOCUMENTS

| | | | |
|---|---|---|---|
| 3,080,287 A | 3/1963 | Lewenstein | 167/65 |
| 4,017,614 A | 4/1977 | Wild | 424/232 |
| 4,585,866 A | 4/1986 | Fozard et al. | 546/129 |
| 4,758,433 A | 7/1988 | Johnson et al. | 424/195.1 |
| 5,053,396 A | 10/1991 | Blass | 514/45 |
| 5,273,759 A | 12/1993 | Simmons | 424/465 |
| 5,538,959 A | 7/1996 | Mauskop | 514/165 |
| 5,972,916 A | 10/1999 | Armellino et al. | 514/165 |

OTHER PUBLICATIONS

Goadshy, "Mechanisms and management of headache," Journal of the Royal College of Physicians of London, vol. 33, No. 3, May/Jun. 1999, pp 228–234.

Lipton et al., "Migraine in the United States: A review of epidemiology and health care use," Neurology 43 (Suppl 3) Jun. 1993, pp S6–S10.

Stewart et al., "Migraine heterogeneity Disability pain intensity,and attack frequency and duration," Neurology 44(Supp 4) Jun. 1994, pp S24–S39.

Rasmussen et al., "Impact of headache on sickness absence and utilisation of medical services: a Danish population study," Journal of Epidemiology and Community Health 1992;46, pp 443–446.

Lipton et al., "Undiagnosed Migraine Headaches A Comparison of Sympton–Based and Reported Physican Diagnoisis," Arch Intern Med–Vol 152, Jun. 1992, pp 1273–1278.

Edmeads et al., "Impact of Migraine and Tension–Type Headache on Life–Style, Consulting Behavior, and Medication Use: A Canadian Population Survey," Le Journal Canadien Des Sciences Neurologiques, 1993; 20, pp 131–137.

Rasmussen et al., "Epidemiology of Migraine," The Headaches, Second Edition, pp 227–234 (2000).

Olesen, "A review of current drugs of migraine,"Journal of Neurology (1991) 238, pp S23–S27.

Solomon, "Therapeutic Advances in Migraine," J Clin Pharmacol 1993; 33, pp 200–209.

Laska et al., "Caffeine as an Analgesic Adjuvant," The Journal of the American Medical Association, Apr. 6, 1984, Vol 251, No. 13, pp 1711–1718.

Schmidt et al., "Effect of Caffeine on Intestinal Absorption of Ergotamine in Man," Europ. J. Clin. Pharmacol. 7 (1994), pp 213–216.

Stang et al., "Migraine Patterns of healthcare use," Neurology 1994; 44 (Suppl 4), pp S47–S55.

Stewart et al., "Prevalence of Migraine Headache in the United States Relation to Age Income, Race, and Other Sociodemographic Factors," JAMA, Jan. 1, 1992–Vol 267, No. 1, pp 64–69.

Deleu et al., "Symptomatic and Prophylactic Treatment of Migraine: A Critical Reappraisal," Clinical Neuropharmacology, vol. 21, No. 5, pp 267–269 (1998).

Clissold, "Paracetamol and Phenacetin," Drugs 32 (Suppl. 4) (1986), pp 46–59.

Hughes et al., "Review Articles Effects of Pseudoephedrin in Man," Journal of Clinical and Hospital Pharmacy (1983) 8, pp 315–321.

Munari et al, "Pharmacologic Evaluation of Cardiovasular Reflex Responses in Mirgraine Patients:Lack of Central Sympathetic Modulation?", Functional Neurology 4(4) 1989, pp 375–378.

Diamond, "Head Pain Diagnosis and Management," Clinical Symposia, Ciby–Geigy Corporation, vol. 46, No. 3, 1994, pp 1–34.

Lipton, et al., "Over The Counter Medication and the Treatment of Migraine," Headache 1994; 34, pp 547–548.

Migliardi et al., "Caffeine as an analgesic adjuvant in tension headache," Clinical Pharmacology & Therapeutics, vol. 56, No. 5, pp 576–586 (1994).

Sawynok, "Pharmacological Rationale for the Clinical Use of Caffeine," Drugs 49(1) 1995, pp 37–50.

Celanto et al., "Medication Use and Disability Among Migraineurs: A National Probability Sample Survey," Headache 1992; 32, pp 223–228.

Lipton et al., "Medicalo Consultation for Migraine: Results of the AASH–Gallup Survey," and Lipton et al., "Gastrointestinal Symptoms in Migraine: Results from the AASH– Gallup Survey," Additional Posters Presented at the Annual Meeting of AASH, Jun. 23–25, (1995) Boston, Massachusetts, p 563.

(List continued on next page.)

Primary Examiner—Dwayne C. Jones
Assistant Examiner—C. Delacroix-Muirheid
(74) Attorney, Agent, or Firm—Hodgson Russ LLP

(57) ABSTRACT

This invention is a safe and effective composition and method for treating acute migraine attacks using pseudoephedrine, acetaminophen, and other agents in an orally administrated form to alleviate the pain and cluster of symptoms characteristic of migraine attacks such as nausea, photophobia, phonophobia, and functional disabilities as well as the prodrome phase of a migraine attack.

18 Claims, No Drawings

OTHER PUBLICATIONS

Lipton et al., *"Headache 287P Medical Consultation for Migraine,"* Neurology 44 (Suppl. 2) Apr. 1994.
"Pseudoephedrine," Clinical Pharmacology on Physicians' Online, pp 1–2, No Date Given.
"Caffeine," Clinical Pharmacology on Physicians' Online, pp 1–2, No Date Given.
"Acetaminophen," Clinical Pharmacology on Physicians' Online, pp 1–3, No Date Given.
"Acetaminophen, Pseudoephedrine," Clinical Pharmacology on Physicians'pp 1–3, No Date Given.
"Acetaminophen; Caffeine," Clinical Pharmacology on Physicians' Online pp 1–2, No Date Given.
"Caffeine," Clinical Pharmacology on Physicians' Online,, pp 1–3, No Date Given.

MIGRAINE MEDICINE AND METHOD FOR TREATING SAME

This application relies on the priority of provisional patent application Serial No. 60/144,973 which was filed on Jul. 22, 1999.

FIELD OF THE INVENTION

The present invention relates generally to compositions and methods used to alleviate the symptoms and pain associated with an acute migraine attack.

BACKGROUND OF THE INVENTION

An estimated 24 to 26 million Americans—about 18% of women and 6% of men—suffer from migraine pain and migraine-related symptoms. (Stewart W F, Lipton R B, Celentano D D, Reed M L. Prevalence of migraine headache in the United States: relation to age, income, race, and other sociodemographic factors. JAMA 1992; 267:64–69.) Attacks are common, with more than 32% of sufferers experiencing more than four episodes per month. (Rasmussen B K, Stewart W F. The Epidemiology of Migraine. In: Olesen J, Tfelt-Hansen P, Welch K M A, editors. The Headaches, second edition. New York, N.Y.: Raven Press; 2000; p. 227–233.)

Migraine, a heterogeneous disorder, produces a wide spectrum of pain and associated disabilities, both within and among individual sufferers. The spectrum includes mild pain and no disability in approximately 5–15% of migraine attacks, moderate to severe pain and disability in approximately 60–70% of attacks, and incapacitating pain and total disability in the remaining approximately 25–35% of attacks. (Stewart W F, Schecter A, Lipton R B. Migraine heterogeneity: disability, pain intensity, and attack frequency and duration. Neurology 1994; 44 Suppl 4:S24–S39 and Lipton R B, Stewart W F. Migraine in the United States: A review of epidemiology and health care use. Neurology 1993; 43 Suppl 3:S6–S10.)

Recent population-based epidemiological studies in the United States and elsewhere, have found that most people with migraines are not currently consulting a physician for their migraine attacks, and only about one-third have ever been diagnosed by a doctor. (Edmeads J, Findlay H, Tugwell P, Pryse-Phillips W, Nelson R F, Murray T J. Impact for migraine and tension-type headache on lifestyle, consulting behavior and medication use: a Canadian population survey. Can J Neurol Sci. 1993; 20:131–137; Lipton R B, Stewart W F. Medical consultation for migraine [abstract]. Neurology 1994; 44 Suppl 2:A199; and Rasmussen B K, Jensen R, Olesen J. Impact of migraine on sickness, absence and utilization of medical services: a Danish population study. J Epidemiol Community Health 1992; 46:443–446.) The overwhelming majority (95% of men and 97% of women) of migraineurs, i.e., individuals who suffer from migraines, used medication to assuage their pain, although only about 28% of the men and 40% of the women have ever used prescription medications. (Lipton R B, Stewart W F, Celentano D D, Reed M L. Undiagnosed migraine: A comparison of symptom-based and physician diagnosis. Arch Int Med 1992; 152:1273–1278; and Celentano D D, Stewart W F, Lipton R B, Reed M L. Medication use and disability among migraineurs: a national probability sample survey. Headache 1992; 32:223–228.) More than 90% of migraineurs use nonprescription medication for their migraines and the majority use nonprescription medications exclusively. (Stang P E, Osterhaus J T, Celentano D D. Migraine: patterns of healthcare use. Neurology 1994; 44 Suppl 4:S47–S55; and Edmeads J, Findlay H, Tugwell P, Pryse-Phillips W, Nelson R F, Murray T J. Impact for migraine and tension-type headache on lifestyle, consulting behavior and medication use: a Canadian population survey. Can J Neurol Sci. 1993; 20:131–137.)

Many migraine sufferers use single-agent nonprescription analgesics such as acetaminophen, or aspirin, or non-steroidal anti-inflammatory agents to treat their attacks. (Lipton R B, Newman L C, Solomon S. Over-the-counter medication and the treatment of migraine. Headache 1994; 34:547–548.) In other countries, a number of nonprescription drugs are specifically approved for migraine pain. (Lipton R B, Newman L C, Solomon S. Over-the-counter medication and the treatment of migraine. Headache 1994; 34:547–548.) The effectiveness of self-treatment of a migraine and the effectiveness of most such nonprescription drugs in relieving or aborting migraine pain and/or the characteristic symptoms of a migraine has not been adequately studied in well-controlled clinical trials. (Lipton R B, Newman L C, Solomon S. Over-the-counter medication and the treatment of migraine. Headache 1994; 34:547–548.) Acetaminophen, aspirin, and caffeine are approved for relief of nonspecific headaches and tension headaches (Migliardi J R, Armellino J J, Friedman M, Gillings D B, Beaver W T. Caffeine as an analgesic adjuvant in tension headache. Clin Pharmacol Ther 1994; 56:576–586), which are clinical and physiologically distinct from a migraine.

Caffeine is widely consumed and has also been indicated for use to treat asthma, drowsiness, fatigue, lumbar puncture headache, and neonatal apnea. [(Reents S. Clinical Pharmacology. Gold Standard Multimedia, Inc. (www.gsm.com) 1999. Available from URL:https://home.po.com.)] Caffeine is also an analgesic adjuvant for a variety of pain conditions and has been included in combination with other analgesics, ergot alkaloids, and barbiturates in prescription formulations for a migraine. (Laska E M, Sunshine A, Mueller F, Elvers W B, Siegel C, Rubin A. Caffeine as an analgesic adjuvant. JAMA 1984; 251:1711–1718; Olesen J. A review of current drugs for migraine. J Neurology 1991; 238 Suppl 1:S23–S27; Solomon G D. Therapeutic advances in migraine. J Clin Pharmacol 1993; 33:200–209; and Sawynok J. Pharmacological rationale for the clinical use of Caffeine. Drugs 1995; 49:37–50.) Caffeine itself may act to relieve a migraine. Caffeine has shown to reduce cerebral blood flow in humans and to be a nonselective adenosine receptor antagonist. Reduction of cerebral blood flow may be due to caffeine inhibition of the adenosine A2 receptor. (Sawynok J. Pharmacological rationale for the clinical use of Caffeine. Drugs 1995; 49:37–50.) A2 receptors are on cerebral vascular muscles, and act to cause vasodilation. Hence, their inhibition would have the effect of vasoconstriction similar to other medications used to abort the migraine headache.

Although the symptom pattern varies among migraine sufferers, the severity of migraine pain justifies a need for vigorous therapy in the great majority of cases. Traditional therapy, such as ergotamine, although effective during the prodrome phase of a migraine attack, is known to become progressively less effective if its administration is delayed. Ergotamine is frequently combined with caffeine, a known analgesic adjuvant, to facilitate absorption of the ergot alkaloid. (Schmidt R, Fanchamps A. Effect of Caffeine on intestinal absorption of ergotamine in man. Eur J Clin Pharmacol 1974; 57:213–216.) However, repeated dosing of ergotamine induces long-lasting and cumulative vasoconstriction, thereby requiring careful instructions and management of individuals who take oral preparations for migraine attack.

Because of the cumulative toxicity of ergotamine and its derivatives, safer therapeutics for the treatment and prophylaxis of migraines have been sought. Examples of such ergotamine alternatives are ergonovine, propranolol, and methysergide. Significant toxicity, however, also occurs in nearly 40% of the individuals who take these agents. A prescription anti-migraine medication that is an alternative to ergotamine and its derivatives is sumatriptan (or sumatriptan succinate), which is a selective 5-hydroxytryptamine. (Deleu D, Hanssens Y, Worthing E. Symptomatic and prophylactic treatment of migraine: a critical reappraisal. Clin Neuropharmacol 1998; 21(5) :267–279; and Stewart W F, Lipton R B, Celentano D D, Reed M L. Prevalence of migraine headache in the United States: relation to age, income, race, and other sociodemographic factors. JAMA 1992; 267:64–69.) When given early, anti-migraine medications effectively abort the acute symptoms of a migraine attack and the prodrome symptoms. Most of these medications, such as ergotamine, its derivatives, and selective 5-hydroxytryptamine agonists, share the physiological property of causing vasoconstriction. (Deleu D, Hanssens Y, Worthing E. Symptomatic and prophylactic treatment of migraine: a critical reappraisal. Clin Neuropharmacol 1998; 21(5):267–279.)

Thus, a clear goal in the art is to discover new, safe, nontoxic, and effective anti-migraine drugs and treatments, particularly nonprescription treatment medications that can be self-administered without the need of a medical prescription.

SUMMARY OF THE INVENTION

The present invention relates to a medicinal composition for treating individuals afflicted with pre-migraine conditions, migraine-associated symptoms, and/or migraine pain of mild to severe intensity. The medicinal composition comprises at least pseudoephedrine and acetaminophen and is orally administrated.

DETAILED DESCRIPTION OF THE PRESENT INVENTION

In general, the migraine condition, with or without aura, has a variety of characteristic features. Migraine attacks are episodic and self-limited. The duration of untreated or unsuccessfully treated migraine attacks can be from several hours to several days (e.g., about four hours to about three days). Common pain characteristics of migraines include pain in a unilateral location, with a pulsating quality. Pain is usually of moderate to severe intensity and is aggravated by routine physical activity. One or more of a cluster of symptoms is recognized to frequently accompany migraines, namely, nausea and/or vomiting, photophobia, phonophobia, and functional disability, i.e., difficulty in performing routine work-related and non-work-related tasks.

The prodrome phase of a condition of migraine occurs before aura and before severe or throbbing migraine pain. Frequently during prodrome, the migraine sufferer experiences mood changes, lethargy, and tiredness. It will also be appreciated that migrainous aura, which is experienced by about 20% of migraine sufferers, precedes severe migraine pain and throbbing. Aura involves distinctive auditory and visual distortions, which may involve visual scotomas or even hemianopia and speech abnormalities, which develop prior to severe migraine pain and throbbing.

Medicinal treatment of migraine condition can be done during the prodrome phase, or in the aura phase (when it occurs), which are known to precede an acute migraine attack and migraine pain. Generally, the acute medicinal treatment is more effective in the prodrome phase. However, most acute medicinal treatments for migraine such as the present invention can be administered during the prodrome to abort the migraine attack or during the migraine attack once the migraine pain and its other symptoms have developed in order to reduce or eliminate migraine pain and its associated symptoms.

As stated above, the present invention relates to a medicinal composition for treating individuals afflicted with pre-migraine conditions, migraine-associated symptoms, and/or migraine pain of mild to severe intensity. The medicinal composition comprises at least pseudoephedrine and acetaminophen and is orally administrated. Each component of this medicinal composition must be shown to be safe and useful in treating the migraine complex, and evidence shows that the ingredients of the combination can work synergistically to treat a migraine. For example, one additional component that can be added to the medicinal composition which adds synergistic effect is caffeine.

The ingredients of the combination medication of pseudoephedrine, acetaminophen, and caffeine act synergistically. Caffeine has been shown to act synergistically with acetaminophen to produce analgesia, (Sawynok J. Pharmacological rationale for the clinical use of Caffeine. Drugs 1995; 49:37–50.) and to enhance the action of other medications such as ergotamine in relieving acute migraine attacks by increasing its absorption. (Schmidt R, Fanchamps A. Effect of Caffeine on intestinal absorption of ergotamine in man. Eur J Clin Pharmacol 1974; 57:213–216).

As stated previously, caffeine itself may act to relieve the migraine. Caffeine has shown to reduce cerebral blood flow in humans and to be a nonselective adenosine receptor antagonist. Reduction of cerebral blood flow may be due to caffeine inhibition of the adenosine A2 receptor. (Sawynok J. Pharmacological rationale for the clinical use of Caffeine. Drugs 1995; 49:37–50.) A2 receptors are on cerebral vascular muscles, and act to cause vasodilation. Hence, their inhibition would have the effect of vasoconstriction similar to other medications used to abort the migraine headache.

The large arteries at the base of the brain and the pia mater arteries make up the innervated vascular system of the cerebral vessels, which has a rich adrenergic nerve supply and responds to catecholamines. These vessels would vasoconstrict in response to sympathomimetic drugs such as pseudoephedrine. The non-innervated vascular system is connected serially to the first, consisting of parenchymal arteries and terminal high resistance arterioles. The newer theories about pathogenesis of migraine complex describe that in susceptible individuals trigger factors set off a series of local and systemic events that initiate both focal and generalized manifestation of the migraine. Generally, an initial vasoconstriction phase occurs locally and predominantly in the unilateral cerebral vessels. This unilateral vasoconstriction is associated with aura in cases of a classic migraine. The vasoconstriction is followed by reflex vasodilation due to local anoxia, acidosis, and systemic drop in serotonin. Marked vasodilation with accumulated vasoactive substances sensitizes the pain receptors in the blood vessels and produces a sterile inflammation. These changes along with the vasodilation cause the pain in migraine. (Seymour D. Head Pain Diagnosis and Management. Clin Symp 1994; 46(3):2–34.)

Abortion of a migraine headache is thought to be achieved by vasoconstriction of dilated intracranial and extracranial vessels since vasodilation is associated with the headache phase. (Seymour D. Head Pain Diagnosis and Management. Clin Symp 1994; 46(3):2–34.; Godsby P J. Mechanism and management of headache. J R Coll Physicians Lond May/June 1999; 33(3):228–234; and Sawynok J. Pharmacological rationale for the clinical use of Caffeine. Drugs 1995; 49:37–50.) Vasoconstriction produces reduction in blood flow. For example ergotamine and sumatriptan produce vasoconstriction of cranial blood vessels. (Deleu D, Hanssens Y, Worthing E. Symptomatic and prophylactic treatment of migraine: a critical reappraisal. Clin Neuropharmacol 1998; 21(5):267–279.) The termination of the headache is achieved 1) by restoring the loss of homeostasis of blood supply to the brain to reduce the sterile inflammation caused by vasodilation and 2) by reducing the vasodilated vessels closer to a normal state that would directly decrease the sensation of pain in the innervated vessels.

Caffeine and pseudoephedrine may have a synergistic affect on cerebral vasoconstriction, since pseudoephedrine acts as an agonist directly on both alpha and, to the lesser degree, beta-adrenergic receptors. [(Reents S. Clinical Pharmacology. Gold Standard Multimedia, Inc. (www.gsm.com) 1999. Available from URL:https://home.po.com.)] Activation of alpha-adrenergic receptors on vascular smooth muscles causes vasoconstriction. (Seymour D. Head Pain Diagnosis and Management. Clin Symp 1994; 46(3) :2–34.)

Acetaminophen has been routinely used to treat mild to moderate migraines. (Godsby PJ. Mechanism and management of headache. J R Coll Physicians Lond May/June 1999; 33(3): 228–234; and Deleu D, Hanssens Y, Worthing E. Symptomatic and prophylactic treatment of migraine: a critical reappraisal. Clin Neuropharmacol 1998; 21(5) :267–279.)

Turning to the present invention and study, a hand full of migraine patients were treated privately with the combination of pseudoephedrine 60 mg and acetaminophen 1000 mg every six (6) hours. These patients reported a reduction of their migraine symptoms such as headache, nausea, phonophobia, and photophobia in 2 hours after treatment, as compared to acetaminophen alone. Most cases of migraine attack were completely aborted after one to two treatments (see table 1).

TABLE 1

| Age | Sex | Severity of headache on a scale of 1–10, before the medication | Severity of headache on a scale of 1–10, after the medication | Other symptoms besides headache | Relief of other symptoms achieved |
|---|---|---|---|---|---|
| 29 | M | 8 | Completely relieved | Photo and Phono | All relieved |
| 34 | M | 6 | Completely relieved | Photo, nausea, and Phono | All relieved |
| 31 | F | 9.5 | Completely relieved | Photo, nausea, and Phono | All relieved |

Notes on table 1:
Age is given in years.
M = male.
F = female.

Medication is pseudoephedrine 60 mg and acetaminophen 1000 mg, given once, after one episode of a migraine attack.

Photo=photophobia.
Phono=phonophobia.
Nausea

Pseudoephedrine has been shown to be effective in treating migraine patient's cardiovascular abnormalities. A study was done on cardiovascular reflex response in migraine patients. (Munari L, Milaneri I, Silvani A, Bussone G, Bioardi A., Pharmacologic evaluation of cardiovascular reflex responses in migraine patients: lack of central sympathetic modulation. Funct. Neurol. 1989; 4(4): 375–378.) Pretreatment with 2 mg/kg abolished the effects of lower blood pressure after sustained handgrip that is seen in migraine patients versus normal patients. This was statistically significant data (p<0.05). Pretreatment with 2 mg/kg abolished effects of increased postural hypotension that is seen in migraine patients versus normal patients. This was statistically significant data (p<0.05).

The components of this medication are relatively safe and with few side effects. Each component of this medication has been available as an over-the-counter medication in the US for other uses than the scope of this invention.

The uses of the combination pseudoephedrine and acetaminophen have included treatment of the symptoms associated with common cold, nasal congestion, sinus congestion, and sinus pain symptoms, but not migraine symptoms. [(Reents S. Clinical Pharmacology. Gold Standard Multimedia, Inc. (www.gsm.com) 1999. Available from URL:https://home.po.com.)] Some examples of the brand names of these types of medication are Sudafed® Sinus Maximum, Alka-Seltzer® Plus Cold-Sinus Medicine Liqui-Gels, Infants' Tylenol® Cold Decongestant & Fever Reducer, and Excedrin® Sinus.

Acetaminophen has been widely used since the 1950s. Acetaminophen has been used alone for arthralgia, dental pain, dysmenorrhea, fever, headache, mild pain, myalgia, and osteoarthritis. Although, acetaminophen has been used for migraine pain, it has not been used in combination with pseudoephedrine or pseudoephedrine and caffeine. Acetaminophen has proven to be safe and with very few side effects compared to the group of NSAID analgesics. (Clissold S P., Pharacetamol and phenacetin. Drugs 1986; 32 Suppl 4: 315–321.)

Also, pseudoephedrine has been widely used and shown to be safe and with few side effects. Pseudoephedrine has been mainly used to treat nasal congestion. (Hughes DTD, Empey D W, Land M. Effects of pseudoephedrine in man. Journal of Clinical and Hospital Pharmacy 1983; 8:315–321.)

Caffeine is widely consumed and has also been indicated for use to treat asthma, drowsiness, fatigue, lumbar puncture headache, and neonatal apnea. [(Reents S. Clinical Pharmacology. Gold Standard Multimedia, Inc. (www.gsm.com) 1999. Available from URL:https://home.po.com.)]

The length of time that acetaminophen, pseudoephedrine, and caffeine have been on the market with relatively few side effects has demonstrated their excellent safety profiles.

The present invention is the medicinal composition for treatment of migraine complex symptoms. The medicinal composition is an oral medication of pseudoephedrine and acetaminophen, or pseudoephedrine, acetaminophen, and caffeine. Such oral formulations would be in a liquid, solid, or gelatin (semi-solid) form such as an elixir, pill, or capsule. Without limiting the scope of the present invention, an oral dosage of the combination medication may, for example, compromise:

EXAMPLE 1

A single solid or liquid dosage form comprise of pseudoephedrine in an amount of from about 30 mg to about 60 mg, acetaminophen in an amount of from about 200 mg to about 1000 mg, and caffeine in an amount of about 40 mg to about 100 mg; or

EXAMPLE 2

A single solid or liquid dosage form comprise of pseudoephedrine in an amount of from about 30 mg to about 60 mg, and acetaminophen in an amount of from about 200 mg to about 1000 mg.

The dosage specified in Examples 1 and 2 can be taken every 6 hours by mouth. This dosage is in agreement with the over-the-counter recommended dosages of the pseudoephedrine, acetaminophen, and caffeine.

Without limiting the scope of the present invention, in the composition of these vehicles to administrate the active medications of pseudoephedrine and acetaminophen, and pseudoephedrine, acetaminophen, and caffeine, acceptable additives may be added if desired. The acceptable additives may be in the group of glidants, lubricants, disintegrating agents, coloring agents, and fillers. Examples of these acceptable additives are pregelatinized starch, magnesium stearate, microcrystalline cellulose, croscarmellose sodium, D&C yellow #10, and colloidal silicon dioxide.

In conclusion, the present invention relates generally to compositions and methods used to alleviate the symptoms and pain associated with acute migraine attacks. More particularly, the present invention relates to the use of a combination of pseudoephedrine and acetaminophen with optional caffeine, and is orally administrated for treating individuals afflicted with pre-migraine conditions, migraine-associated symptoms, and/or migraine pain of mild to severe intensity. The combination pseudoephedrine and acetaminophen with optional caffeine is a new, effective, and convenient medication to treat acute migraine attacks. Each of the ingredients of this combination has been shown to be useful in treating the migraine complex. Evidence shows that the ingredients of the medicinal combination work synergistically to treat migraine.

While preferred embodiments of the present invention have been disclosed, it will be appreciated that it is not limited thereto but may be otherwise embodied with the scope of the following claims.

I claim:

1. A method for treating migraine pain and the cluster of symptoms characteristic of a migraine attack, the symptoms selected from the group consisting of nausea, photophobia and phonophobia, comprising the steps of administering to a human subject a composition comprising a combination of pseudoephedrine, acetaminophen and caffeine in an amount effective to reduce or eliminate the migraine pain and one or more of said symptoms characteristic of migraine.

2. The method according to claim 1, wherein two or more of said symptoms characteristic of migraine are reduced.

3. The method according to claim 1, wherein said composition is administered in a solid oral dosage form.

4. The method according to claim 3, wherein said dosage form is selected from the group consisting of tablets, pills, caplets, and capsules.

5. The method according to claim 3, wherein one solid dosage form comprises pseudoephedrine in an amount of from about 30 mg to about 60 mg, acetaminophen in an amount of from about 200 mg to about 1000 mg, and caffeine in an amount of about 40 mg to about 100 mg.

6. The method according to claim 5, wherein two solid dosage forms are administered to the human subject about every four to six hours.

7. The method according to claim 6, wherein the composition is not re-administered to the human subject more frequently than once every six hours.

8. The method according to claim 5, wherein the composition is not re-administered to the human subject more frequently than once every six hours.

9. The method according to claim 1, wherein the amount of composition administered is effective to reduce the migraine pain and two or more of said symptoms characteristic of migraine.

10. The method according to claim 1, wherein the amount of composition administered is effective to reduce the migraine pain and all three of said symptoms characteristic of migraine.

11. The method according to claim 1, wherein said composition is administered in a liquid oral dosage form.

12. The method according to claim 11, wherein one liquid dosage form comprises pseudoephedrine in an amount of from about 30 mg to about 60 mg, acetaminophen in an amount of from about 200 mg to about 1000 mg, and caffeine in an amount of about 40 mg to about 100 mg.

13. The method according to claim 11, wherein two liquid dosage forms are administered to the human subject about every four to six hours.

14. The method according to claim 11, wherein the composition is not re-administered to the human subject more frequently than once every six hours.

15. A method of aborting a migraine attack, wherein the migraine attack is characterized by symptoms including nausea, photophobia and phonophobia, comprising administering to a human subject during the prodrome phase of the migraine attack a migraine abortive effective amount of a composition comprising a combination of pseudoephedrine, acetaminophen, and caffeine.

16. A method for treating migraine pain and nausea characteristic of a migraine attack comprising the step of administering to a human subject a composition comprising a combination of pseudoephedrine, acetaminophen, and caffeine in an amount effective to reduce the migraine pain and nausea characteristic of a migraine attack.

17. A method for treating migraine pain and photophobia characteristic of a migraine attack comprising the step of administering to a human subject a composition comprising a combination of pseudoephedrine, acetaminophen, and caffeine in an amount effective to reduce the migraine pain and photophobia characteristic of a migraine attack.

18. A method for treating migraine pain and phonophobia characteristic of a migraine attack comprising the steps of administering to a human subject a composition comprising a combination of pseudoephedrine, acetaminophen, and caffeine in an amount effective to reduce the migraine pain and phonophobia characteristic of a migraine attack.

* * * * *

UNITED STATES PATENT AND TRADEMARK OFFICE
CERTIFICATE OF CORRECTION

PATENT NO. : 6,642,243 B1
DATED : November 4, 2003
INVENTOR(S) : Imanzahrai

It is certified that error appears in the above-identified patent and that said Letters Patent is hereby corrected as shown below:

<u>Title page,</u>
Item [*] Notice, should read as follows:
-- Subject to any disclaimer, the term of this patent is extended or adjusted under 35 U.S.C. 154(b) by 153 days. --

Signed and Sealed this

Seventeenth Day of February, 2004

JON W. DUDAS
*Acting Director of the United States Patent and Trademark Office*